United States Patent [19]

Inoue

[11] Patent Number: 5,262,140

[45] Date of Patent: Nov. 16, 1993

[54] PROCESS FOR PRODUCING AN ALKALINE EARTH METAL BORATE DISPERSION

[75] Inventor: Kiyoshi Inoue, Hiratsuka, Japan

[73] Assignee: Nippon Oil Co., Ltd., Tokyo, Japan

[21] Appl. No.: 878,772

[22] Filed: May 5, 1992

Related U.S. Application Data

[63] Continuation of Ser. No. 563,032, Aug. 6, 1990, abandoned.

[30] Foreign Application Priority Data

Aug. 9, 1989 [JP] Japan .................. 1-204887

[51] Int. Cl.$^5$ .............................. C01B 35/00
[52] U.S. Cl. .................... 423/286; 423/290; 252/33.6; 252/39; 252/49.6
[58] Field of Search ........... 423/286, 290; 252/33.6, 252/39, 49.6

[56] References Cited

U.S. PATENT DOCUMENTS

| | | | |
|---|---|---|---|
| 4,668,409 | 5/1987 | Yamaguchi et al. | 252/32.7 E |
| 4,683,126 | 7/1987 | Inoue et al. | 423/280 |
| 4,734,211 | 3/1988 | Kennedy | 252/51.5 A |
| 4,744,920 | 5/1988 | Fischer et al. | 252/33.4 |
| 4,965,004 | 10/1990 | Schlicht et al. | 252/38 |
| 5,013,463 | 5/1991 | Slama | 252/18 |
| 5,064,545 | 11/1991 | Steckel | 252/32.7 HC |
| 5,102,569 | 4/1992 | Onopchenko et al. | 252/49.6 |
| 5,160,652 | 11/1992 | Small, Jr. et al. | 252/49.6 |

FOREIGN PATENT DOCUMENTS

1239421 7/1988 Canada .

Primary Examiner—Gary P. Straub
Assistant Examiner—Timothy C. Vanoy
Attorney, Agent, or Firm—Bucknam and Archer

[57] ABSTRACT

A process for producing an alkaline earth metal borate dispersion, comprising the two steps of:

(1) reacting a mixture of (A) an oil-soluble alkaline earth metal salt, (B) an alkaline earth metal hydroxide or oxide, (C) a boric acid or anhydride, (D) an alkanol of 1 to 4 carbon atoms, (E) water and (F) a diluent at 20° to 120° C., and (2) removing the water and optionally part of the alkanol and/or the diluent from the reaction mixture by heating it.

6 Claims, No Drawings

PROCESS FOR PRODUCING AN ALKALINE EARTH METAL BORATE DISPERSION

This is a continuation of application Ser. No. 563,032, filed Aug. 6, 1990 which was abandoned on Jun. 5, 1992.

BACKGROUND OF THE INVENTION

1. Field of the Invention

This invention relates to a process for producing an alkaline earth metal borate dispersion, more particularly to a process for producing an alkaline earth metal borate dispersion containing homogeneously dispersed very fine alkaline earth metal borate.

2. Prior Art

A boron compound serves to improve the oxidation stability, rust-preventing properties, friction reducing properties and extreme pressure properties of a lubricating oil. Further, it has recently been found that an alkaline earth borate has excellent acid neutralizing properties and excellent hydrolytic stability when compared with conventional calcium carbonate. Under such circumstances, many research workers have attempted to incorporate stably a boron compound in the form of an alkaline earth metal borate in a lubricating oil. Especially, processes for stabilizing an alkaline earth metal borate in the form of ultramicroparticles in an oil by using a metallic detergent, for example, an alkaline earth metal sulfonate or an alkaline earth metal salicylate as a protective colloid have been studied.

For example, U.S. Pat. No. 3,679,584 discloses a process comprising reacting an overbased alkaline earth metal carbonate, namely, an overbased alkaline earth metal sulfonate with boric acid and an alkaline earth metal hydroxide in a mineral oil or a diluent by heating while blowing carbon dioxide into the reaction system. Further, U.S. Pat. Nos. 3,829,381, 4,744,920, etc., disclose processes comprising reacting an overbased alkaline earth metal sulfonate with boric acid in a mineral oil. Furthermore, Can. Pat. No. 1,239,421 discloses a process for reacting an alkaline earth metal carbonate overbased compound, namely, an overbased alkaline earth metal salicylate with boric acid in a diluent by heating.

Since these processes comprise the use of a lubricating oil additive based on an overbased alkaline earth metal carbonate as a starting material, it is necessary for producing a lubricating oil additive based on an overbased alkaline earth metal borate that the reaction be conducted in at least two stages, namely, making a neutral metallic detergent overbased and then reacting the overbased detergent with boric acid. On the other hand, the inventor of the present invention disclosed in Japanese Patent Laid-Open No. 204298/1986 that an alkaline earth metal borate overbased sulfonate could be produced by reacting water with boric acid and an alkaline earth metal hydroxide or oxide by heating in an oil solution a neutral alkaline earth metal sulfonate, namely, by a one-stage reaction.

However, it turned out that the process disclosed in the Japanese Patent Laid-Open No. 204298/1986 could not provide any product of a high total base number, namely, a high-boron content product when it was applied to the production of an alkaline earth metal borate overbased salicylate or phenolate, though it was suitable for the production of an alkaline earth metal borate overbased sulfonate.

SUMMARY OF THE INVENTION

It is an object of this invention to provide a simple process for producing an alkaline earth metal salt dispersion, namely, an alkaline earth metal borate overbased salicylate, phenolate or catecholate dispersion having a very small particle diameter and a large boron to alkaline earth metal molar ratio and excelling in detergent dispersion properties, extreme pressure properties, friction and abrasion resistance, corrosion preventing properties, rust preventing properties, hydrolytic stability and acid neutralizing properties by a one-stage reaction.

To accomplish the abovementioned object, the inventor of this invention has made intensive studies on a process for producing alkaline earth metal borate overbased salicylate, phenolate and catecholate, and has found out that they can be obtained at a high boron content by a specified production process, thus accomplishing this invention.

Namely this invention provides a process for producing an alkaline earth metal borate dispersion, comprising the two steps of:

(1) reacting a mixture of
  (A) 100 parts by weight of at least one oil-soluble alkaline earth metal salt selected from the group consisting of an oil-soluble neutral alkaline earth metal salicylate, an oil-soluble neutral alkaline earth metal phenolate and an oil-soluble alkaline earth metal catecholate with
  (B) 10 to 200 parts by weight of an alkaline earth metal hydroxide or oxide,
  (C) 0.5 to 6.5 moles, per mole of component B, of a boric acid or anhydride,
  (D) 20 to 1000 parts by weight of an alkanol of 1 to 4 carbon atoms,
  (E) 1 to 40 parts by weight of water and
  (F) 40 to 1000 parts by weight of a diluent at 20° to 120° C., and
(2) removing the water and optionally part of the alkanol and/or the diluent from the reaction mixture by heating it to 100° to 200° C.

DETAILED DESCRIPTION OF THE INVENTION

This invention will now be described in more detail.

Component A mentioned in step (1) (hereinafter referred to as the reaction step) of this invention is at least one oil-soluble alkaline earth metal salt selected from an oil-soluble neutral alkaline earth metal salicylate (normal salt), an oil-soluble neutral alkaline earth metal phenolate (normal salt) and an oil-soluble neutral alkaline earth metal catecholate (normal salt), and more particularly a salt of an alkaline earth metal such as magnesium, calcium or barium with an alkylsalicylic acid, an alkylphenol or an alkylcatechol of a molecular weight of about 200 to 500 can be used. Examples of these compounds include those prepared by the production processes disclosed in Japanese Patent Laid-Open No. 101196/1985, Japanese Patent Publication No. 35325/1973 and U.S. Pat. No. 4,668,409.

Component B mentioned in the reaction step of this invention is an alkaline earth metal hydroxide or oxide, and examples thereof include magnesium hydroxide, calcium hydroxide, barium hydroxide, magnesium oxide, calcium oxide, and barium oxide. The kind of the alkaline earth metal of component B may be the same as or different from that of component A.

The amount of component B used in the reaction step is 10 to 200 parts by weight, desirably 20 to 100 parts by weight per 100 parts by weight of component A.

Component C mentioned in the reaction step of this invention is a boric acid. Examples thereof include orthoboric acid, metaboric acid, tetraboric acid and boric anhydride. Generally orthoboric acid is desirable. The amount of component C used in the reaction step is 0.5 to 6.5 moles, desirably 1.0 to 6.0 moles per mole of component B.

Component D mentioned in the reaction step of this invention is an alkanol having 1 to 4 carbon atoms. A desirable component D is a monoalkanol or a dialkanol, and examples thereof include methanol, ethanol, propanol, butanol, ethylene glycol, propylene glycol, triethylene glycol, butylene glycol, tetramethylene glycol and mixtures thereof. The amount of component D used in the reaction step is 20 to 1000 parts by weight, desirably 60 to 600 parts by weight per 100 parts by weight of component A.

Component E mentioned in the reaction step of this invention is water. By mixing the water with the abovementioned component D at an appropriate ratio in the reaction step, the formed alkaline earth metal borate particles become very fine, and the amount of coarse particles to be removed in the final filtration step can be decreased. The amount of component E used in the reaction step is 1 to 40 parts by weight, desirably 2 to 20 parts by weight per 100 parts by weight of component A.

Component F mentioned in the reaction step of this invention is a diluent, and a nonpolar organic solvent of a boiling point of 60° C. or higher can be usually used. Examples of the diluent include aromatic hydrocarbons such as benzene, toluene and xylene, petroleum-derived solvents such as benzine, ligroin, mineral spirit and cleaning solvents and a gasoline fraction, a kerosene fraction, a gas oil fraction and a lubricating oil fraction of a mineral oil. It is to be noted that component F includes the mineral oil used as a dispersion medium for component A, i.e., a neutral alkaline earth metal salicylate, a neutral alkaline earth metal phenolate, and a neutral alkaline earth metal catecholate.

The amount of component F used in the reaction step of this invention is 40 to 1000 parts by weight, desirably 200 to 600 parts by weight per 100 parts by weight of component A.

Although the diluent as component F is used from the beginning as a dispersion medium for component A in the form of a mixture thereof with component A, it is also possible to add, if necessary, a diluent which is the same as or different from this dispersion medium in the reaction step.

In the reaction step of this invention, specified amounts of the abovementioned components A to F are reacted with each other under agitation at a reaction temperature of 20° to 100° C., preferably 40° to 95° C. In this invention, the reaction is desirably carried out at atmospheric pressure in the abovementioned reaction temperature range. Although the reaction time is arbitrary, it is usually 2 to 8 hours, desirably 3 to 5 hours.

The reaction mixture obtained in this way is subjected to the subsequent step (2) (hereinafter referred to as the distillation step). While agitating the reaction mixture, the system is heated to 100° to 200° C., desirably 110° to 160° C. and kept at that temperature for usually 1 to 2 hours to remove the water from the system. In this distillation step, the water added as component E in the reaction step and the water formed by the reaction can be removed while the extent of hydration of the formed alkaline earth metal borate can be suitably regulated. It is also possible to remove part of the alkanol as component D or the diluent as component E or the both in this step, if required.

The alkaline earth metal borate dispersion obtained through the abovementioned reaction and distillation steps may be further purified, if necessary, by means of filtration or the like in order to remove remaining unreacted material and coarse particles of the alkaline earth metal borate.

The alkaline earth metal borate dispersion obtained by the process of this invention usually contains 5 to 30 wt. % of the alkaline earth metal borate. This content can be freely varied by varying the mixing ratio of the alkaline earth metal hydroxide or oxide as component B and the boric acid as component C to the neutral alkaline earth metal salicylate, neutral alkaline earth metal phenolate or neutral alkaline earth metal catecholate as component A in the reaction step.

Further the alkaline earth metal borate dispersion has a boron to alkaline earth metal molar ratio as high as about 0.8 to 6% according to the overall compositional analysis. This boron originates in component C of this invention, while the alkaline earth metal originates in components A and B. It is a prominent feature of this invention that an alkaline earth metal borate dispersion having such a high boron to alkaline earth metal molar ratio can be obtained.

The particle diameter of the alkaline earth metal borate obtained by the process of this invention is 1000 Å or below, usually 500 Å or below, desirably 200 Å or below. It is another prominent feature of the process of this invention that an alkaline earth metal borate having such a small particle diameter can be obtained.

EFFECTS OF THE INVENTION

According to this invention, it is possible, as described above, to obtain an alkaline earth metal borate dispersion by a very simple one-stage reaction. As mentioned above, the obtained alkaline earth metal borate dispersion has a freely variable alkaline earth metal borate content, a high boron to alkaline earth metal molar ratio and further a very small particle diameter.

Further the alkaline earth metal borate dispersion has excellent detergent dispersing properties, friction and abrasion resistance, extreme pressure properties, rust preventing properties, corrosion preventing properties, acid neutralizing properties and hydrolytic stability, so that it can be used as such or in the form diluted with a suitable solvent as an additive for petroleum products such as fuels and lubricating oils or as a rust preventive for corrosion-resistant paints or the like.

EXAMPLES

This invention will now be described in more detail with reference to Examples and Comparative Examples.

EXAMPLE 1

A solution of 100 parts by weight of a neutral calcium alkylphenolate (A) in 100 parts by weight of a lubricating oil fraction, 24 parts by weight of calcium hydroxide (B), 40 parts by weight (2.0 moles per mole of the calcium hydroxide) of orthoboric acid (C), and 400 parts by weight of xylene (F) were put in a 1000-ml four-necked flask fitted with a condenser and heated to 40° C. under agitation. To this mixture was added 200 parts by weight of methanol (D) and 4 parts by weight of water (E), and the resulting mixture was heated under agitation to the reflux temperature (66° C.) and reacted for 3 hours. The reaction mixture was further heated to 140° C. to distill out the methanol, water and xylene. Finally the reaction product was diluted twofold with hexane and filtered, and the hexane was distilled out to leave the desired calcium borate over based alkylphenolate.

This alkylphenolate had the following analytical values:

Ca: 7.2 wt. %
B: 5.5 wt. %
total base number: 207 (JIS K 2501, 5.2.3)

EXAMPLE 2

A solution of 100 parts by weight of a neutral calcium alkylsalicylate (A) in 100 parts by weight of a lubricating oil fraction, 24 parts by weight of calcium hydroxide (B), 40 parts by weight (2.0 moles per mole of the calcium hydroxide) of orthoboric acid (C) and 400 parts by weight of xylene (F) were put in a 1000-ml four-necked flask fitted with a condenser and heated to 40° C. under agitation. To this mixture was added 64 parts by weight of methanol (D) and 4 parts by weight of water (E) and the resulting mixture was heated under agitation to the reflux temperature (66° C.) and reacted for 3 hours. The reaction mixture was further heated to 140° C. to distill out the methanol, water and xylene. Finally the reaction product was diluted twofold with hexane and filtered, and the hexane was distilled out to leave the desired calcium borate overbased alkylsalicylate.

This alkylsalicylate had the following analytical values:

Ca: 6.2 wt. %
B: 4.9 wt. %
total base number: 187 (JIS K 2501, 5.2.3)

COMPARATIVE EXAMPLE 1

A solution of 100 parts by weight of a neutral calcium alkylphenolate (A) in 100 parts by weight of a lubricating oil fraction, 24 parts by weight of calcium hydroxide (B), 40 parts by weight (2.0 moles per mole of the calcium hydroxide) of orthoboric acid and 400 parts by weight of xylene (F) were put in a 1000-ml four-necked flask fitted with a condenser, and heated under agitation to 40° C. To this mixture was added 4 parts by weight of water (E), and the resulting mixture was heated under agitation to the reflux temperature (90° C.) and reacted for 3 hours. The reaction mixture was further heated to 140° C. to distill out the water and xylene. Finally the reaction product was diluted twofold with hexane and filtered, and the hexane was distilled out to leave the desired calcium borate overbased alkylphenolate.

This alkylphenolate had the following analytical values:

Ca: 3.2 wt. %
B: 0.9 wt. %
total base number: 89 (JIS K 2501, 5.2.3)

COMPARATIVE EXAMPLE 2

A solution of 100 parts by weight of a neutral calcium alkylsalicylate (A) in 100 parts by weight of a lubricating oil fraction, 24 parts by weight of calcium hydroxide (B), 40 parts by weight (2.0 moles per mole of the calcium hydroxide) of orthoboric acid and 400 parts by weight of xylene (F) were put in a 1000-ml four-necked flask fitted with a condenser, and heated under agitation to 40° C. To this mixture was added 4 parts by weight of water (E), and the resulting mixture was heated under agitation to the reflex temperature (90° C.) and reacted for 3 hours. The reaction mixture was further heated to 140° C. to distill out the water and xylene. Finally the reaction product was diluted twofold with hexane and filtered, and the hexane was distilled out to leave the desired calcium borate overbased alkylsalicylate.

This alkylsalicylate had the following analytical values:

Ca: 2.9 wt. %
B: 1.8 wt. %
total base number: 85 (JIS K 2501, 5.2.3)

The results of Comparative Examples 1 and 2 clearly indicate that when no alkanol as component D of this invention was used, each of the obtained alkaline earth metal borate dispersions had a smaller total base number than those obtained by the production process of this invention and had poor performances as an additive.

COMPARATIVE EXAMPLE 3

A solution of 100 parts by weight of neutral calcium alkylsalicylate (A) in 100 parts by weight of a lubricating oil fraction, 24 parts by weight of calcium hydroxide (B), 40 parts by weight of orthoboric acid (2.0 moles per mole of the calcium hydroxide), and 400 parts by weight of xylene (F) were put in a 1000-ml four-necked flask fitted with a condenser, and heated under agitation to 40° C. To this mixture was added 64 parts by weight of methanol (D), and the resulting mixture was heated under agitation to the reflux temperature (66° C.) and reacted for 3 hours. The reaction mixture was further heated to 140° C. to distill out the methanol and the xylene. Finally the reaction product was diluted twofold with hexane and filtered, and the hexane was distilled out. The gelation of the mixture occurred, so that no desired calcium borate overbased alkylsalicylate could be obtained.

What is claimed is:

1. A process for producing an additive for petroleum products which consists of an overbased alkaline earth metal borate dispersion consisting of two steps of:
   (1) reacting a mixture of
      (A) 100 parts by weight of an oil-soluble neutral alkaline earth metal salicylate, with
      (B) 10 to 200 parts by weight of an alkaline earth metal hydroxide or oxide,
      (C) 0.5 to 6.5 moles, per mole of component B, of orthoboric acid, metaboric acid, tetraboric acid or boric anhydride,
      (D) 60 to 200 parts by weight of an alkanol of 1 to 4 carbon atoms,
      (E) 1 to 40 parts by weight of water and
      (F) 40 to 1000 parts by weight of a diluent which is a nonpolar organic solvent of boiling point of 60° C. or higher when the reaction temperature is 20° to 120° C. for 2 to 8 hours, and
   (2) removing the water in a distillation step from the reaction mixture by heating it to 100° to 200° C. for 1 to 2 hours.

2. The process according to claim 1 wherein said diluent is benzene, toluene, xylene, ligroin, mineral spirit, gasoline, kerosene, gas oil or a lubricating oil.

3. The process according to claim 1 wherein in said step (2) said alkanol or said diluent or both said alkanol and said diluent are also removed.

4. The process according to claim 1 wherein said overbased alkaline earth metal borate dispersion contains 5-30% by weight of the alkaline earth metal borate.

5. The process according to claim 1 wherein said overbased alkaline earth metal borate dispersion has boron to alkaline earth metal, molar ratio of 0.8-6%.

6. The process according to claim 1 wherein in the overbased alkaline earth metal borate dispersion the particle diameter is not greater than 1000-Å.

* * * * *